United States Patent [19]
Chu

[11] Patent Number: 5,958,423
[45] Date of Patent: *Sep. 28, 1999

[54] MODIFIED LIVE BRSV VACCINE

[75] Inventor: Hsien-Jue Chu, Fort Dodge, Iowa

[73] Assignee: American Home Products Corporation, Madison, N.J.

[*] Notice: This patent is subject to a terminal disclaimer.

[21] Appl. No.: 08/993,400

[22] Filed: Dec. 18, 1997

Related U.S. Application Data

[63] Continuation of application No. 08/638,879, Apr. 25, 1996, Pat. No. 5,733,555, which is a continuation of application No. 08/240,373, May 10, 1994, abandoned.

[51] Int. Cl.$^6$ ...................... A61K 39/295; A61K 39/155; A61K 39/245
[52] U.S. Cl. ...................... 424/202.1; 424/211.1; 424/218.1; 424/229.1
[58] Field of Search .............. 424/204.1, 202.1, 424/211.1, 218.1, 229.1, 279.1, 280.1, 278.1

[56] References Cited

U.S. PATENT DOCUMENTS

| | | | |
|---|---|---|---|
| 4,772,466 | 9/1988 | Allison et al. | 424/209.1 |
| 5,733,555 | 3/1998 | Chu | 424/211.1 |

FOREIGN PATENT DOCUMENTS

| | | |
|---|---|---|
| 0 129 923 | 1/1985 | European Pat. Off. . |

OTHER PUBLICATIONS

Kimman et al., 1987, *J. Clinical Microbiol.* 25(6): 1097–1106.
Stott et al., 1984, *J. Hyg. Camb.* 93: 251–261.
Thomas et al., 1986, *Agri–Practice* 7: 26–30.
Syvrud et al., 1988, *Vet. Med.* 83: 429–430.
Gillette, K.G., 1983, *Am. J. Vet. Res.* 44(12): 2251–2225.
Elazhary, M.A.S.Y., 1984, *Am. J. Vet. Res.* 45(8): 1660–1662.
Baker, John C. et al., 1986, *Am. J. Vet. Res.* 47(2): 246–253.
Kelling, C., 1993, *Veterinary Medicine.* 88:903–906.
Baker, John C., 1985, *Dissertation Abstracts Int.* 45: 2463–B.
Bohiender, Robert E., 1984, *Modern Veterinary Practice,* 60:606–609.
Kucera et al., 1983, *Agri–Practice, Vet. Med.* 78: 1599–1604.
Baker, J. et al., 1986, *Bovine Vet. Forum* 1 No. 2: 2–16.
T.G. Kimman et al., 1989, *Vet. Immunol. Immunopathol.* 22, 2: 145–160.
J.C. Baker, 1991, *Vet. Q* 13, 1: 47–59.
A.C. Allison, et al., 1990, *Semin. Immunol.* 2, 5: 369–374.
Rosenthal, Maurice L., Jan. 1996, ROBANE® and SUPRAENE® a ROBECO Inc. publication: 647–675.

*Primary Examiner*—Terry McKelvey
*Attorney, Agent, or Firm*—Darby & Darby

[57] ABSTRACT

The invention provides an improved BRSV vaccine composition, which advantageously provides immunity from infection after a single administration. The composition comprises a modified live BRS virus and an adjuvant, which in combination provide immunity from BRSV infection after a single administration, and elicit an immune response specific to BRSV and including cell-mediated immunity and local (secretory IgA) immunity. In a preferred embodiment, the BRS virus is strain 375, and the adjuvant comprises an unsaturated turpin hydrocarbon, preferably squalene or squalane, and a polyoxypropylene-polyoxyethylene block copolymer, most preferably one where the copolymer has a polyoxypropylene (POP) component with an average molecular weight of about 3250 to 4000 and the polyoxyethylene (POE) component comprises about 10–20% of the total molecule. The adjuvant may optionally include a surfactant, preferably a polyoxyethylenesorbitan monooleate.

10 Claims, No Drawings

MODIFIED LIVE BRSV VACCINE

This is a continuation of application Ser. No. 08/638,879, filed Apr. 25, 1996, now U.S. Pat. No. 5,733,555 which is a continuation of U.S. application Ser. No. 08/240,373, filed May 10, 1994, now abandoned. Each of these prior applications is hereby incorporated herein by reference, in its entirety.

FIELD OF THE INVENTION

This invention pertains to improved methods for inducing protective immunity against Bovine Respiratory Syncytial Virus (BRSV), specifically employing a modified live vaccine suitable for administration to recipient animals in a single dose.

BACKGROUND TO THE INVENTION

Bovine Respiratory Syncytial Virus (BRSV) is now recognized as an important etiologic agent in the Bovine Respiratory Disease Complex (BRDC). Disease is characterized by rapid breathing, coughing, loss of appetite, ocular and nasal discharge, and elevated temperatures. In an acute outbreak, death may follow within 48 hours of onset of symptoms.

BRSV infects cattle of all ages, including nursing calves. BRSV is considered the most common viral pathogen in enzootic pneumonia in calves, and has also been associated with pulmonary emphysema among newly weaned calves. Thus, there is a need for effective prophylaxis against this virus in cattle and dairy herds.

Establishing protective immunity against BRSV is problematic. As in some other virally-mediated diseases, the levels of serum antibodies against BRSV do not necessarily correlate with protection against disease. This phenomenon may reflect a role for locally produced IgA directed against BRSV (Kimman et al., J. Clin.Microbiol. 25: 1097–1106, 1987), and/or a requirement for cell-mediated immunity to mount an effective defense against this virus. Establishing protective immunity in nursing calves presents additional obstacles, since maternal antibodies to BRSV may deplete the injected immunogen and effectively neutralize the vaccine. Finally, the inconvenience and expense of multiple vaccinations makes a single-dose vaccine desirable. Thus there is a need in the art for one-dose BRSV vaccine formulations that elicit a vigorous and multi-faceted immune response.

The standard administration regimen for prior art BRSV vaccines is two doses (Stott et al., J. Hyg.Camb. 93: 251–261, 1984; Thomas et al., Agri-Practice 5: 1986; and Syvrud et al., Vet.Med. 83: 429–430, 1988; Veterinary Pharmaceuticals & Biologicals, Edition 8 1993/94, pp. 484, 740–741, 956–960, 982–983.) As shown in Kucera et al. (Agri-Practice, Vet.Med., Vol. 78, October 1983, pp. 1599–1604, 1983), a single experimental BRSV vaccination induced relatively low levels of serum neutralization (SN) antibody titer to BRSV, whereas two doses of the vaccine elicited 1:10 to 1:320 SN antibody titers. Furthermore, in herds apparently exposed to BRSV during field trials, approximately 48% of non-vaccinated animals required treatment for respiratory disease, compared with 27% and 21% among single-dose and double-dose vaccinates, respectively. However, the causative agent for respiratory disease in the field trials was not conclusively shown to be BRSV. Also, it was noted that a single-dose vaccine did not appear to be very immunogenic. Later evaluations concluded that two doses of this vaccine would be essential to obtain good protection (Bovine Vet.Forum 1: No.2 pp. 2–16, 1986; Syvrud, et al., Vet.Med. 429–430, 1988).

European Patent Application No.129,923 (published Feb. 1, 1985 and issued as a patent Jul. 9, 1988) describes a method of preparing a live BRSV vaccine that involves dissolving the live vaccine in an inactivated vaccine containing one or more antigens (particularly inactivated influenza virus) formulated as an oil-in-water emulsion. A serological response was obtained in young animals still having maternal immunity. The application also describes a modified-live preparation including BRSV and adjuvant. However, no data were presented on the protective efficacy of any BRSV vaccine against BRSV challenge.

One object of the invention is to provide an effective vaccine against BRSV that elicits protective immunity and prevents disease caused by this virus.

A further object of the invention is to provide an adjuvant suitable for use in a BRSV vaccine, wherein the adjuvant enhances the immunogenicity of the virus so as to elicit protective immunity after a single dose of the vaccine.

SUMMARY OF THE INVENTION

The invention encompasses a composition for enhancing immune responses comprising a block copolymer, such as a polyoxypropylene-polyoxyethylene (POP-POE) block copolymer, preferably Pluronic® L121 (e.g. U.S. Pat. No. 4,772,466), and an organic component, such as a metabolizable oil, e.g. an unsaturated turpin hydrocarbon, preferably squalane (2,6,10,15,19,23-hexamethyltetracosane) or squalene. The composition may also include a non-ionic detergent or surfactant, preferably a polyoxyethylene monooleate such as a Tween® detergent, e.g. Tween®-80.

In this stock adjuvant mixture, the block copolymer, organic oil, and surfactant may be present in amounts ranging from about 10 to about 40 ml/L, about 20 to about 80 ml/L, and about 1.5 to about 6.5 ml/L, respectively. In a preferred embodiment of the stock adjuvant, the organic component is squalane present in an amount of about 40 mL/L, the surfactant is polyoxyethylenesorbitan monooleate (Tween®-80) present in an amount of about 3.2 ml/L, and the POP-POE block copolymer is Pluronic® L121 present in an amount of about 20 mI/L. Pluronic® L121 is a liquid copolymer at 15–40° C., where the polyoxypropylene (POP) component has a molecular weight of 3250 to 4000 and the polyoxyethylene (POE) component comprises about 10–20%, preferably 10%, of the total molecule.

In another aspect, the present invention provides an immunogenic composition for immunizing an animal against infection by Bovine Respiratory Syncytial Virus (BRSV), comprising a modified live BRS Virus combined with the above adjuvant and a pharmaceutically acceptable stabilizer, carrier or diluent. The adjuvant is present in this vaccine composition at a final concentration of about 1–25% (v/v), preferably 5% (v/v). The composition may also include other viruses, such as Infectious Bovine Rhinotracheitis Virus (IBRV), Bovine Viral Diarrhea (BVDV), and Parainfluenza 3 (PI-3V), and may be administered by intramuscular or subcutaneous routes.

In still another aspect, the present invention provides a method for protecting an animal against disease caused by Bovine Respiratory Syncytial Virus, by administering a single dose of the above vaccine comprising modified-live BRSV and adjuvant.

DETAILED DESCRIPTION OF THE INVENTION

All patents, patent applications, and other literature cited herein are hereby incorporated by reference in their entirety. In the case of inconsistencies, the present disclosure will prevail.

As used herein, a "modified live vaccine" is a vaccine comprising a virus that has been altered, typically by passaging in tissue culture cells, to attenuate its ability to cause disease, but which maintains its ability to protect against disease or infection when administered to animals.

"Adjuvant" means a composition comprised of one or more substances that enhances the immunogenicity and efficacy of BRSV when combined with BRSV in a vaccine composition.

An "infectious unit" of BRSV is defined as a $TCID_{50}$, or the amount of virus required for infecting or killing 50% of tissue culture cells.

The present invention provides a vaccine against BRSV that is suitable for single-dose administration. The vaccine is of the modified live virus variety. This provides the advantage of preserving the immunogenicity and/or efficacy of the virus while reducing its virulence.

The vaccine may be prepared from freshly harvested viral cultures by methods that are standard in the art (see Example 1 below.) That is, the virus may be propagated in tissue culture cells such as human diploid fibroblasts or preferably MDBK (Madin-Darby Bovine Kidney) or other bovine cells. The growth of the virus is monitored by standard techniques (observation of cytopathic effect, immunofluorescence or other antibody-based assays), and harvested when a sufficiently high viral titer has been achieved. The viral stocks may be further concentrated or lyophilized by conventional methods before inclusion in the vaccine formulation. Other methods, such as those in described in Thomas, et al., Agri-Practice, V.7 No. 5, pp.26–30., can be employed.

The vaccine of the present invention comprises the modified live virus combined with one or more pharmaceutically acceptable stabilizers, carriers and adjuvants. Carriers suitable for use include saline, phosphate-buffered saline, Minimal essential media (MEM), or MEM with HEPES buffer. Stabilizers include but ar not limited to sucrose, gelatin, peptone, digested protein extracts, such as NZ-Amine or NZ-Amine AS. In particular, the present invention includes an adjuvant that enhances the immunogenicity of the modified live virus and provides for a single administration to elicit protective immunity.

Non-limiting examples of suitable adjuvants include squalane and squalene (or other oils of animal origin); block copolymers such as Pluronic® (L121) Saponin; detergents such as Tween®-80; Quil® A, mineral oils such as Drakeol® or Marcol®, vegetable oils such as peanut oil; Corynebacterium-derived adjuvants such as corynebacterium parvum; Propionibacterium-derived adjuvants such as Propionibacterium acne; Mycobacterium bovis (Bacillus Calmette and Guerinn, or BCG); interleukins such as interleukin 2 and interleukin-12; monokines such as interleukin 1; tumor necrosis factor; interferons such as gamma interferon; combinations such as saponin-aluminum hydroxide or Quil®-A aluminum hydroxide; liposomes; iscom adjuvant; mycobacterial cell wall extract; synthetic glycopeptides such as muramyl dipeptides or other derivatives; Avridine; Lipid A; dextran sulfate; DEAE-Dextran or DEAE-Dextran with aluminum phosphate; carboxypolymethylene, such as Carbopol®; EMA; acrylic copolymer emulsions such as Neocryl® A640 (e.g. U.S. Pat. No. 5,047,238); vaccinia or animal poxvirus proteins; subviral particle adjuvants such as orbivirus; cholera toxin; dimethyidiocledecylammonium bromide; or mixtures thereof.

The formulation of a preferred adjuvant mixture is described in Example 2 below.

The vaccine of the present invention can be administered preferably by intramuscular or subcutaneous routes, or less preferably by intranasal, intraperitoneal, or oral routes.

For single-dose administration, the vaccine should contain an amount of BRSV corresponding to from about $10^{3.0}$ to about $10^{6.0}$ $TCID_{50}$/ml, preferably $10^4$ to $10^5$ $TCID_{50}$/ml. About one to five ml, preferably 2 ml, may be administered per animal, intramuscularly, subcutaneously, or intraperitoneally. One to ten ml, preferably 2 to 5 ml, may be administered orally or intranasally.

The following examples are intended to further illustrate the invention without limiting its scope.

EXAMPLE 1

Growth and Harvesting of BRSV

A) Dpscription of viral stocks: BRSV may be obtained from any number of readily available sources. In one embodiment, BRSV strain 375 may be used. This virulent strain of BRSV originated from Iowa State University, Ames Iowa. Any suitable BRSV strain is contemplated and included within the invention. Similarly, BHV-1, BVDV, and PI-3V are readily available viruses. When obtained in virulent form, these viruses can be attenuated, by known means, to provide modified-live viruses suitable for vaccine use. The viruses can also be killed by conventional methods to provide inactivated viruses suitable for vaccine use. Methods of attenuating or inactivating viruses for vaccine use are well known. Modified-live and/or killed BRSV, BHV-1, BVDV, and PI-3V virus vaccines are known and commercially available See, for example, Thomas, et al., supra, and Veterinary Pharmaceuticals & Biologicals, supra and Appendix 2, A-31–45.

B) Cell culture: The MDBK (NBL-1) cell line, free of BVD, was purchased from the American Type Culture Collection. It was maintained in OptiMEM (Gibco, Grand Island, N.Y.), supplemented with up to 10% (v/v) bovine serum, up to 0.5% lactalbumin hydrolysate (JRH, Lenexa, Kans.), up to 30 mcg/ml polymixin B (Phizer, NY, N.Y.) and neomycin (Upjohn, Kalamazoo, Mich.), and up to 2.5 mcg/ml amphotericin B (Sigma Chemical Co., St. Louis Mo.) Sodium pyruvate, sodium bicarbonate, glucose, L-glutamine and calcium chloride may also be added as required to sustain cell growth.

For virus propagation, OptiMEM, Eagle's MEM, Medium 199, or equivalent medium is supplemented with up to 2% bovine serum, up to 0.5% bovine serum albumin, up to 0.5% lactalbumin hydrolysate, up to 30 mcg/ml polymyxin B and neomycin, and up to 2.5 mcg/ml amphotericin B. Sodium pyruvate, sodium bicarbonate, glucose, L-glutamine and calcium chloride may also be added as required to sustain cell growth.

C) Inoculation of cultures: Individual subconfluent cultures of MDBK cells were inoculated with BRSV, BVDV, PI-3V, or BHV-1V using a multiplicity of infection of 1:5 to 1:5,000 infectious units per cell. The growth medium of the cells was discarded and replaced with viral propagation medium (see above), after which the seed virus was added directly to the culture vessel. The virally-infected cultures were maintained at 36° C.

Viral growth was determined by microscopic examination of cytopathic effect or by fluorescent antibody staining. For BRSV, infected cells showed the formation of syncytia and elongated fusiform cells, which progressed until essentially the complete cell sheet was involved. For BHV-1V, infected cells exhibit cytoplasmic granulation followed by rounding and/or ballooning of infected cells. For BVDV, infected cells form intracellular vacuoles, round up, and leave circumscribed areas devoid of cells. The cytopathic changes in PI-3V-infected cells are similar to those in BHV-1 V-infected cells.

D) Harvesting of Virus: Culture fluids were harvested into sterile vessels. Multiple harvests may begin when 50% of the cell sheet displays characteristic cytopathology, and continue until 100% of the cells are affected. The virus fluids may or may not be clarified by centrifugation or filtration. Viral fluids are stored at −50° C. or colder, or are lyophilized and stored at 2 to 8° C.

For preparation of a final vaccine, viral stocks, either alone or in combination, are mixed with adjuvant.

When liquid viral stocks are used, 19 parts viral stock are mixed with one part adjuvant, preferably the adjuvant of Example 2. When lyophilized viral stocks are used, a dilute 5% (v/v) solution of adjuvant in saline is prepared (mix 1 part adjuvant with 19 parts saline). The lyophilized viral stock is reconstituted (rehydrated) with the diluted adjuvant to form the final vaccine composition. Thimerisol may be added to the final formulation, to a final concentration of 1:10,000.

EXAMPLE 2

Formulation of a Preferred Stock Adjuvant

A preferred adjuvant for use in the present invention was prepared according to the following formulation:

| | |
|---|---|
| polyoxypropylene-polyoxyethylene block copolymer (e.g. Pluronic ® L121; BASF, Parsippany, NJ) | 20 ml |
| Squalane (e.g., Kodak, Rochester, NY) | 40 ml |
| polyoxyethylenesorbitan monooleate (e.g. Tween ® -80, Sigma Chemical, St. Louis, MO) | 3.2 ml |
| buffered salt solution (e.g. D-V PAS Solution, Ca, Mg Free) | 936.8 ml |

The ingredients are mixed and homogenized until a stable mass or emulsion is formed. Prior to homoginization, the ingredients or mixture can be autoclaved. The emulsion may be further sterilized by filtration. Formalin may be added up to a final concentration of 0.2%. Thimerosal may be added to a final dilution of 1:10,000.

EXAMPLE 3

Enhancement of a Modified Live BRSV Vaccine

For this study, two BRSV vaccines were prepared, one with and one without the adjuvant mixture described in Example 2. The vaccine lacking adjuvant contained 2.52 log infectious units of BRSV per 2 ml, while the vaccine containing adjuvant contained 2.96 log infectious units per 2 ml and 5% (v/v) adjuvant.

Each of twenty cattle received a 2-ml dose of vaccine lacking adjuvant, ten intramuscularly and ten subcutaneously. Five additional cattle received a 2-ml dose of vaccine containing adjuvant. All vaccinations were repeated at 21 days. Serum samples were obtained on the sixth day following the second vaccination, and were tested for the presence of anti-BRSV serum neutralization antibodies. The serum neutralization antibody assay is described in Example 4.

The results of this study indicated that 4 of the 5 calves inoculated with the adjuvant-containing BRSV vaccine showed evidence of anti-BRSV antibodies (seroconversion), while none of the twenty animals inoculated with adjuvant-lacking BRSV vaccine showed evidence of antibodies. This indicates that the adjuvant described in Example 2 has the property of enhancing the immunogenicity of modified live BRSV vaccines.

EXAMPLE 4

Single-dose Administration of Improved RRSV Vaccine

The following vaccination and challenge study was performed in order to determine whether a single immunization modified-live Bovine Respiratory Syncytial Virus (BRSV) formulated with an adjuvant would induce protective immunity in cattle. Secondly, the study was designed to determine whether concurrent administration of modified-live Bovine Viral Diarrhea Virus (BVDV), Bovine Herpesvirus, Type 1 (BHV-1 or IBRV), and Bovine Parainfluenza Virus (PI3) would interfere with the induction of protective immunity to BRSV.

A) Experimental Vaccines: Modified-live Bovine Respiratory Syncytial Virus (BRSV) at five passages beyond the master seed was grown on Madin Darby Bovine Kidney (MDBK) cells at master cell stock passage 20. Briefly, MDBK cells were planted in 850 cm$^2$ roller bottles at a density of $3 \times 10^7$ cells per roller bottle in Minimum Essential Media (MEM) containing 5% bovine serum, 0.5% LAH, and 30 µg/mL Gentamycin. Cells were allowed to grow at 37° C. for 2 days prior to infection with virus. Media was decanted from the roller bottles and virus added at a Multiplicity of Infection of 1:600 in 100 mL of virus propagation media per bottle (MEM containing 2% bovine serum, 0.5% LAH, and 30 µg/mL Gentamycin). Seven days after infection, 100% cytopathology was present and supernatant fluids were harvested. The virus was stabilized with 25% (v/v) SGGK3 stabilizer and lyophilized. On the day of vaccination, the lyophilized virus was reconstituted with 5% (v/v) adjuvant diluted in saline diluent (See, Example 2). Reconstituted BRSV virus was combined with PI3, BVDV, and BHV-1 viruses. The titer of each component of the vaccine was determined by replicate titration on the day of vaccination.

B) Experimental Animals Used: A total of 30 cattle were used for this study. These cattle were susceptible to BRSV as indicated by a serum neutralizing (SN) antibody titer of <2 on the day of vaccination for test animals and on the day of challenge for controls. Animals were housed outside with access to a three sided shelter, open to the south. Controls were housed separately from vaccinates prior to challenge in order to avoid exposure to vaccine virus. A complete ration was provided once each day, hay and water were supplied ad libitum.

C) Vaccination: A two mL volume of the combination vaccine was administered once to each vaccinate. Twenty (20) animals were vaccinated (ten by subcutaneous route and ten by intramuscular route) and the remaining ten animals were not vaccinated and served as challenge controls.

D) Experimental Challenge: Animals were challenged with virulent BRSV virus fourteen days following the vaccination. A minimum of $10^{5.7}$ TCID$_{50}$ of virulent BRSV virus was administered to each calf by aerosol challenge on three consecutive days.

E) Clinical Observatinns : Cattle were observed daily from −2 to 14 days following challenge for clinical signs of disease and fever (rectal temperature). Cattle were observed for signs of BRSV infection including, but not limited to, nasal and ocular discharge, conjunctivitis, coughing, dyspnea, anorexia, and depression. Rectal temperature was recorded daily throughout the observation period.

F) Assays:

1. Serum Neutralizing Antibody Assay (SN)

Serial dilutions of heat-inactivated serum were mixed with equal volumes of viral suspensions, in a varying serum-constant virus neutralization test using 100 to 500 $TCID_{50}$ of BRSV. The serum virus mixture was incubated at 37° C. for 1 hour then inoculated onto VERO cells in 96 well microtiter plates. The presence of SN antibody titers was indicated by the absence of virus as detected by cytopathic effect. For the determination of SN antibody titers, 50% neutralization endpoints were calculated according to the method of Reed and Muench.

2. Titration of Virus in Final Dilution of Vaccine

The BRSV virus titer in the vaccine was determined by replicate titration on the day of vaccination. Briefly, the combination vaccine was combined with appropriate neutralizing antisera. The vaccine and antisera mixture was incubated at 37° C. for 45 to 60 minutes. Serial dilutions of the vaccine and antisera were made and inoculated onto VERO cells. The presence of virus was indicated by the presence of cytopathic effect and confirmed by specific immunofluorescence (FA). Virus titer was calculated on each replicate by the method of Reed and Muench. The mean titer of BRSV fraction of the vaccine was $10^{3.4}$ $TCID_{50}$ per dose.

3. Titration of Challenge Virus

The dilution of the BRSV challenge virus administered was serially diluted and inoculated onto MDBK cells in 96 well microtiter plates. The presence of virus was indicated by the presence of cytopathic effect and confirmed by specific immunofluorescence as described for virus isolation.

To interpret the results, clinical scores were assigned as follows:

| Clinical sign | Score/observation |
|---|---|
| Nasal Discharge | |
| Severe serous | 2 |
| Mild mucopurulent | 2 |
| Moderate mucopurulent | 3 |
| Severe mucopurulent | 4 |
| Ocular Discharge | |
| Severe serous | 1 |
| Mild mucopurulent | 2 |
| Moderate mucopurulent | 3 |
| Severe mucopurulent | 4 |
| Conjunctivitis | 2 |
| Coughing | 2 |
| Dyspnea | 2 |
| Anorexia | 1 |
| Hyperemia and reddening of nasal mucosa | 1 |
| Fever (must be at least 1° F. above baseline) | |
| 103.5 to 103.9° F. | 1 |
| 104.0 to 104.9° F. | 2 |
| 105.0 to 105.9° F. | 3 |
| $\geq 106.0°$ F. | 4 |

Mild serous nasal or ocular discharge was considered to be normal for cattle housed outside. Fever was considered significant only if it was at least one degree above the baseline body temperature. The baseline body temperature was determined as the average body temperature for each animal on the day prior to and day of challenge.

Total clinical scores for each animal were summed. Clinical scores of the vaccinates and controls were compared by Mann Whitney Ranked Sum Analysis.

Clinical signs of disease were observed in the control cattle from days 5 through 10 after challenge (Table 1). All of the controls (100%) were observed to have signs of respiratory disease on multiple days. Specific signs of respiratory disease included severe serous nasal discharge (discharge actually dripping from nostril), mucopurulent nasal discharge, ocular discharge, and coughing. The average clinical score for control calves was 3.7.

By comparison, respiratory signs were much less prevalent in vaccinated animals. Only 40% of the vaccinates had any signs of respiratory disease and only two (10%) had clinical signs on multiple days. The average clinical score for the vaccinated group was 1.0. There was a statistically significant reduction in clinical disease in the vaccinates compared to the controls by Mann Whitney Ranked Sum Analysis ($p<0.05$).

These data show that a single-dose administration of adjuvanted modified-live BRSV virus vaccine, according to the invention, provides protection against virulent BRSV challenge. This vaccine and method is effective, even when other vaccines are coadministered with the BRSV vaccine.

Thus, the invention provides a vaccine composition for immunizing an animal against infection by Bovine Respiratory Syncytial Virus (BRSV). The vaccine comprises a modified live BRS Virus, an adjuvant, and a pharmaceutically acceptable carrier, such that the combination provides immunity from BRSV infection after a single administration, and elicits an immune response specific to BRSV and selected from cell-mediated immunity and local (secretory IgA) immunity.

Cell mediated immunity includes the stimulation of T-Helper Cells, T-Killer Cells, and T-Delayed Hypersensitivity Cells, as well as stimulation of macrophage, monocyte, and other lymphokine and interferon production. The presence of cell mediated immunity can be determined by conventional in vitro and in vivo assays. Local immunity, such as secretory IgA, can be determined by conventional ELISA or IFA assays showing a serum neutralizing antibody titer of 1–2 or greater. According to the invention, the cell mediated or local immunity of consequences is specific to or associated with BRSV.

TABLE 1

CLINICAL OBSERVATIONS FOLLOWING BRSV CHALLENGE

CLINICAL OBSERVATIONS ON THE INDICATED DAYS AFTER BRSV CHALLENGE

| Cow ID | Master Tag | V/C | -2 | -1 | 0 | 1 | 2 | 3 | 4 | 5 | 6 | 7 | 8 | 9 | 10 | 11 | 12 | 13 | 14 | Total Score |
|---|---|---|---|---|---|---|---|---|---|---|---|---|---|---|---|---|---|---|---|---|
| 654 | 9612 | C | | | | | | | | | | | | MMN3 | MMN2 | | | | | 5 |
| 685 | 9596 | C | | | | | | | | | | | | MMN2 | SSN2 | | | | | 4 |
| 731 | 9589 | C | | | | | | | | | MMN3 | | | C2 | SSN2 | | | | | 7 |
| 732 | 9579 | C | | | | | | | | SSN2 | | | | | | | | | | 2 |
| 737 | 9575 | C | | | | | | | | | | | | MMS2 | SSN2 | | | | | 4 |

TABLE 1-continued

CLINICAL OBSERVATIONS FOLLOWING BRSV CHALLENGE

CLINICAL OBSERVATIONS ON THE INDICATED DAYS AFTER BRSV CHALLENGE

| Cow ID | Master Tag | V/C | -2 | -1 | 0 | 1 | 2 | 3 | 4 | 5 | 6 | 7 | 8 | 9 | 10 | 11 | 12 | 13 | 14 | Total Score |
|---|---|---|---|---|---|---|---|---|---|---|---|---|---|---|---|---|---|---|---|---|
| 742 | 9580 | C | | | | | | | | | | | | | MMN2 | | | | | 2 |
| 754 | 9578 | C | | | | | | | | | | | | | SSN2 | | | | | 2 |
| 766 | 9586 | C | | | | | | | | | | MMN2 | MMN3 | MMN2 | | | | | | 7 |
| 868 | 9577 | C | | | MD2 | | | | | ,SSO1 | | MMN2, SSO1 | | | | | | | | 5 |
| 871 | 9594 | C | | | | | | C2, | | | | | | | | | | | | 2 |
| 967 | 9600 | C | | | | | | | | | | | | MMN2 | | | | | | 2 |
| 975 | 9585 | C | | | | | | | | | | | | SSN2 | | | | | | 2 |
| 999 | 9576 | C | | | | | | | ,MD2 | | | | | SSN2 | SSN2 | | | | | 6 |
| | | | | | | | | | | | | | | | | | | | AVERAGE | 3.8 |
| 669 | 9512 | M | | | | | | | | | | | | MMN2 | | | | | | 2 |
| 853 | 9729 | M | | | | | | | SSO1 | | | | | | | | | | | 1 |
| 875 | 9754 | M | | | | | | | | | | | | | | | | | | 0 |
| 886 | 9737 | M | | | | | | | | | | | | | | | | | | 0 |
| 895 | 9770 | M | | | | | | | | | | | | | | | | | | 0 |
| 899 | 9723 | M | | | | | | | | | | | | | | | | | | 0 |
| 933 | 9782 | M | | | | | | | | | | | | | | | | | | 0 |
| 934 | 9749 | M | | | | | | | | | | | | | | | | | | 0 |
| 952 | 9779 | M | | | | | | | | | | | | | | | | SSN2 | | 2 |
| 954 | 9725 | M | SD3 | | | | | | | | | | | | | | | | | 0 |
| No Tag | 9735 | M | | | | | | | | | | | | | | | | | | 0 |
| | | | | | | | | | | | | | | | | | | | AVERAGE | 0.5 |
| 717 | 9520 | SQ | | | | | | | | | | | | | | | | | | 0 |
| 835 | 9753 | SQ | | | | | | | | | | | | | | | | | | 0 |
| 840 | 9736 | SQ | | | | | | | | | | | | | | MMN2 | | | | 2 |
| 863 | 9724 | SQ | MD2 | | | | | | | | | | | | | | | | | 0 |
| 872 | 9743 | SQ | | | | | | | | | | | | | | | | | | 0 |
| 881 | 9776 | SQ | | | | | | | | | | | | SSN2 | MMN2 | | | | | 4 |
| 887 | 8775 | SQ | | | | | | | | | | | MMN3 | | MMN2 | MMN2 | | | | 7 |
| 945 | 9750 | SQ | | | | | | | | | | | | | | | | | | 0 |
| 994 | 9719 | SQ | | | | | | | | ,C2 | | | | | | | | | | 2 |
| 996 | 9746 | SQ | | | | | | | | | | | | SSN2 | | | | | | 2 |
| | | | | | | | | | | | | | | | | | | | AVERAGE | 1.7 |
| | | | | | | | | | | | | | | | | ALL VACCINATED AVERAGE | | | 1.0 |

IM = Vaccinated Intramuscularly
C = Control
SQ = Vaccinated Subcutaneous
Ocular Discharge:
SSO1-Severe Serous
MMO2-Mild Mucopurulant
MMO3-Moderate Mucopurulant
SMO4-Severe Mucopurulant
Diarrhea:
MD2-Moderate, Runny
SD3-Severe, Splattered
ED4-Extreme, Explosive
Nasal Discharge:
MSN1-Moderate-Serous
SSN2-Severe Serous
MMN2-Mild Mucopurulant
MMN3-Moderate Mucopurulant
SMN4-Severe Mucopurutant
Coughing-C2
Labored Breathing-LB2
Poor Appetite-PA1
Salivation-S1
Oral Lesions-OL1

I claim:

1. A vaccine composition for immunizing an animal against infection by Bovine Respiratory Syncytial Virus (BRSV) comprising
a modified live BRSV, an adjuvant, and a pharmaceutically acceptable carrier, which composition elicits protective immunity from BRSV infection after a single administration, and elicits a BRSV-specific immune response selected from the group consisting of cell-mediated immunity, secretory immunoglobulin A immunity, and a combination thereof.

2. The composition of claim 1, wherein the adjuvant additionally comprises a surfactant.

3. The composition of claim 1, wherein the adjuvant also comprises a surfactant present in a final concentration of about 0.0015 to 0.20% (v/v).

4. The composition of claim 2 or claim 3, wherein the surfactant is a polyoxyethylene sorbitan monooleate.

5. The composition of claim 1 further comprising a Bovine Rhinotracheitis Virus IV, a Bovine Viral Diarrhea Virus, and a Parainfluenza 3 Virus.

6. A method for protecting an animal against disease caused by BRSV, comprising the step of administering to said animal an immunogenic composition comprising a modified live BRSV, an adjuvant, and a pharmaceutically acceptable carrier, such that, after a single administration, the composition elicits protective immunity from BRSV infection and elicits a BRSV-specific immune response selected from the group consisting of cell-mediated immunity, secretory immunoglobulin A immunity, and a combination thereof.

7. The method of claim 6 wherein said immunogenic composition comprises about $10^3$ to about $10^6$ infectious units per milliliter.

8. The method of claim 6 wherein said administering step comprises one intramuscular, subcutaneous, intraperitoneal, oral, or intranasal administration.

9. The method of claim 6, wherein the adjuvant additionally comprises a non-ionic surfactant in a final concentration of about 0.0015 to 0.20% (v/v).

10. The method of claim 6 or claim 9, further comprising the coadministration of a Bovine Rhinotracheitis Virus IV, a Bovine Viral Diarrhea Virus, and a Parainfluenza 3 Virus.

* * * * *